(12) United States Patent
Sawabe et al.

(10) Patent No.: US 8,535,815 B2
(45) Date of Patent: Sep. 17, 2013

(54) COMPOUND AND ORGANIC LIGHT-EMITTING DIODE, DISPLAY AND LIGHTING DEVICE USING THE SAME

(75) Inventors: Tomoaki Sawabe, Tokyo (JP); Atsushi Wada, Fukuoka (JP); Yukitami Mizuno, Tokyo (JP); Tomoko Sugizaki, Kawasaki (JP); Isao Takasu, Tokyo (JP); Shintaro Enomoto, Yokohama (JP)

(73) Assignee: Kabushiki Kaisha Toshiba, Minato-ku, Tokyo (JP)

( * ) Notice: Subject to any disclaimer, the term of this patent is extended or adjusted under 35 U.S.C. 154(b) by 370 days.

(21) Appl. No.: 13/049,967

(22) Filed: Mar. 17, 2011

(65) Prior Publication Data
US 2012/0056163 A1    Mar. 8, 2012

(30) Foreign Application Priority Data
Sep. 7, 2010  (JP) .................. 2010-200211

(51) Int. Cl.
*H01L 51/54*  (2006.01)
*C09K 11/06*  (2006.01)

(52) U.S. Cl.
USPC ...... 428/690; 428/917; 252/301.16; 313/504; 313/506; 257/40; 257/102; 257/E51.044; 546/2

(58) Field of Classification Search
None
See application file for complete search history.

(56) References Cited

U.S. PATENT DOCUMENTS
2011/0215304 A1  9/2011  Wada
2012/0056162 A1  3/2012  Wada

FOREIGN PATENT DOCUMENTS
JP  2005/089367 A  * 4/2005

OTHER PUBLICATIONS

Del Zotto et al. "Copper(I), silver(I), and gold(I) complexes with the hybrid ligand 1-(diphenylphosphino)-2-(2-pyridine)ethane (ppye). Variable-temperature nuclear magnetic resonance investigations and the crystal structure of [Au(ppye-P)2]FP6." J. Chem. Soc. Dalton Trans. 1995. p. 3343-3351.*
Xia, et al., *"Efficient Electrophosphorescence from Low-Cost Cooper(I) Complex"*, Optical Materials 29, 2007, pp. 667-671.

* cited by examiner

*Primary Examiner* — Michael H Wilson
(74) *Attorney, Agent, or Firm* — Ohlandt, Greeley, Ruggiero & Perle, L.L.P.

(57) ABSTRACT

According to one embodiment, there is provided a compound represented by Formula (1):

[Chem 1]

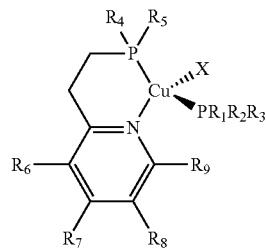

(1)

where Cu represents a copper, $PR_1R_2R_3$ is a phosphine compound coordinating with Cu, where $R_1$, $R_2$, $R_3$, $R_4$ and $R_5$ may be the same or different, and represent a linear, branched or cyclic alkyl group having 1-6 carbon atoms or an aromatic cyclic group which may have a substituent, $R_6$, $R_7$, $R_8$ and $R_9$ each independently represents a halogen atom, cyano group, nitro group, linear, branched or cyclic alkyl group having 1-6 carbon atoms or H, and X is F, Cl, Br or I.

6 Claims, 3 Drawing Sheets

COMPOUND AND ORGANIC LIGHT-EMITTING DIODE, DISPLAY AND LIGHTING DEVICE USING THE SAME

CROSS-REFERENCE TO RELATED APPLICATIONS

This application is based upon and claims the benefit of priority from Japanese Patent Application No. 2010-200211, filed Sep. 7, 2010; the entire contents of which are incorporated herein by reference.

FIELD

Embodiments described herein relate generally to a novel compound, and an organic light-emitting diode, a display and a lighting device using the same.

BACKGROUND

In recent years, organic light-emitting diodes have been attracting attention as a technology for next-generation displays and solid state lighting. In the early study of organic light-emitting diodes, fluorescence has been mainly used. However, in recent years, an organic light-emitting diode utilizing phosphorescence which exhibits higher internal quantum efficiency has been attracting attention.

Mainstream of emissive layers utilizing phosphorescence in recent years are those in which a host material containing an organic material is doped with an emissive metal complex including iridium or platinum as a central metal.

However, an iridium and platinum are rare metals and are therefore expensive, giving rise to the problem that organic light-emitting diodes using these rare metals are increased in cost. Copper complexes, on the other hand, likewise emit phosphorescent light and are inexpensive, so that they are expected to reduce the production cost.

An organic light-emitting diode using a copper complex as a light-emitting material has been disclosed, but the organic light-emitting diode has a problem of a high turn-on voltage. In order to attain energy saving and long lifetime of the organic light-emitting diode, it is preferable to use an emitting dopant which starts emission with a lower applied voltage.

DETAILED DESCRIPTION

According to one embodiment, there is provided a compound represented by Formula (1):

[Chem 1]

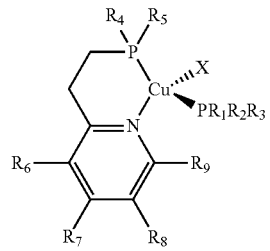

(1)

where Cu represents a copper; PR$_1$R$_2$R$_3$ represents a phosphine compound coordinating with Cu, where R$_1$, R$_2$ and R$_3$ may be the same or different, and represent a linear, branched or cyclic alkyl group having 1-6 carbon atoms or an aromatic cyclic group which may have a substituent; R$_4$ and R$_5$ may be the same or different, and represent a linear, branched or cyclic alkyl group having 1-6 carbon atoms or an aromatic cyclic group which may have a substituent; R$_6$, R$_7$, R$_8$ and R$_9$ each independently represents a halogen atom, cyano group, nitro group, linear, branched or cyclic alkyl group having 1-6 carbon atoms or H; and X represents F, Cl, Br or I.

Embodiments of the present invention are explained below in reference to the drawings.

Figure 1:
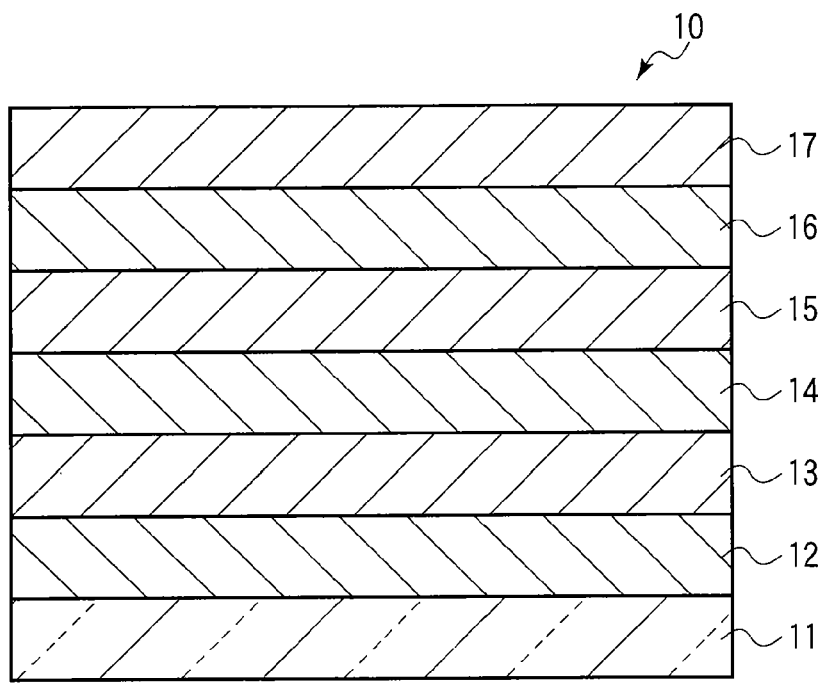
FIG. 1 is a cross-sectional view of an organic light-emitting diode of an embodiment.

FIG. 1 is a cross-sectional view of the organic light-emitting diode of an embodiment of the present invention.

In the organic light-emitting diode 10, an anode 12, hole transport layer 13, emissive layer 14, electron transport layer 15, electron injection layer 16 and cathode 17 are formed in sequence on a substrate 11. The hole transport layer 13, electron transport layer 15 and electron injection layer 16 are formed if necessary.

Each member of the organic light-emitting diode of the embodiment of the present invention is explained below in detail.

The emissive layer 14 receives holes and electrons from the anode and the cathodes, respectively, followed by recombination of holes and electrons which results in the light emission. The energy generated by the recombination excites the host material in the emissive layer. An emitting dopant is excited by energy transfer from the excited host material to the emitting dopant, and the emitting dopant emits light when it returns to the ground state.

The emissive layer 14 contains a luminescent metal complex (hereinafter, referred to as an emitting dopant), which is doped into the host material of an organic material. In this embodiment, a copper complex represented by the following formula (1) is used as an emitting dopant.

[Chem 2]

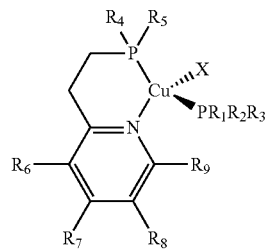

(1)

In the formula, Cu represents a copper. $PR_1R_2R_3$ represents a phosphine compound coordinating with Cu. $R_1$, $R_2$ and $R_3$ may be the same or different, and represent a linear, branched or cyclic alkyl group having 1-6 carbon atoms or an aromatic cyclic group which may have a substituent. Specific examples of the alkyl group include a methyl group, isopropyl group and cyclohexyl group. Specific examples of the above aromatic cyclic group include a phenyl group, naphthyl group and phenoxy group, each of which may be substituted with a substituent such as an alkyl group, halogen atom and carboxyl group. $R_4$ and $R_5$ may be the same or different, and represent a linear, branched or cyclic alkyl group having 1-6 carbon atoms or an aromatic cyclic group which may have a substituent. Specific examples of the alkyl group include a methyl group, isopropyl group and cyclohexyl group. Specific examples of the above aromatic cyclic group include a phenyl group, naphthyl group and phenoxy group, each of which may be substituted with a substituent such as an alkyl group, halogen atom and carboxyl group. $R_6$, $R_7$, $R_8$ and $R_9$ each independently represents a halogen atom, cyano group, nitro group, branched, linear or cyclic alkyl group having 1-6 carbon atoms or H. In the case where $R_6$, $R_7$, $R_8$ or $R_9$ is the alkyl group, specific examples thereof include a phenyl group, naphthyl group, phenoxy group, or the like. X represents F, Cl, Br or I.

The use of the copper complex as the emitting dopant enables the fabrication of an organic light-emitting diode more reduced in cost than in the case of using an iridium complex or platinum complex. Further, the copper complex represented by the above formula (1) can be synthesized more easily than other copper complexes which are known to be used as the emitting dopant.

The copper complex represented by the above formula (1) starts emission with a lower applied voltage as compared to the conventional examples in the case where the copper complex is used as an emitting dopant of an organic light-emitting diode. When an same brightness is obtained with a lower applied voltage than previously possible, a reduction in power consumption is attained, and it is possible to suppress deterioration of materials. Therefore, it is possible to attain energy-saving and long lifetime of the organic light-emitting diode with the use of the copper complex represented by the above formula (1) as compared to the cases of using other copper complexes.

Hereinafter, a synthetic scheme of the copper complex represented by the above formula (1) will be described. In the following reaction formulas, $R_1$, $R_2$, $R_3$, $R_4$, $R_5$, $R_6$, $R_7$, $R_8$, $R_9$ and X are as defined above.

[Chem 3]

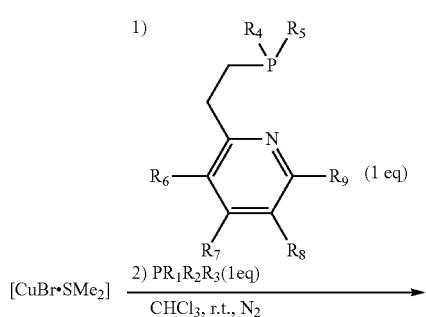

(1)

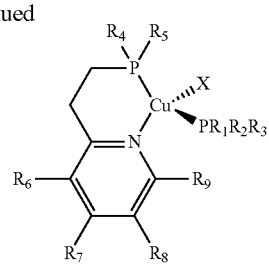

Specific examples of the copper complex represented by the above formula (1) include a copper complex ([CuBr(PyC2PPh$_2$)(PPh$_3$)]) in which a ligand (PyC2PPh$_2$) in which pyridine (py) and diphenylphosphine (PPh$_2$) are linked by an ethylene chain, a triphenylphosphine (PPh$_3$) ligand, and Br coordinates with Cu. A structure of the [CuBr(PyC2PPh$_2$)(PPh$_3$)] is shown below.

[Chem 4]

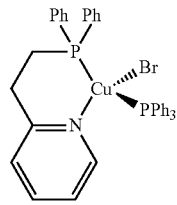

As the host material, a material having a high efficiency in energy transfer to the emitting dopant is preferably used. The host materials used when using a phosphorescent emitting dopant as the emitting dopant are roughly classified into a small-molecular type and a polymer type. An emissive layer containing a small-molecular host material is mainly formed by vacuum co-evaporation of a small-molecular host material and an emitting dopant. An emissive layer containing a polymer host material is formed by applying a solution obtained by blending the polymer host material with the emitting dopant as essential components. Typical examples of the small-molecular host material include 1,3-bis(carbazole-9-yl)benzene (mCP). Typical examples of the polymer host material include a poly(N-vinylcarbazole) (PVK). Besides the above materials, 4,4'-bis(9-dicarbazolyl)-2,2'-biphenyl (CBP), p-bis(triphenylsilyl)benzene (UGH2) and the like may be used as the host material in this embodiment.

In the case of using a host material having high hole-transport ability, the carrier balance between holes and electrons in the emissive layer is not maintained, giving rise to the problem concerning a drop in luminous efficacy. For this, the emissive layer may further contain an electron injection/transport material. In the case of using a host material having high electron-transport ability on the other hand, the emissive layer may further contain a hole injection/transport material. Such a structure ensures a good carrier balance between holes and electrons in the emissive layer, leading to improved luminous efficacy.

A method for forming the emissive layer 14 includes, for example, spin coating, but is not particularly limited thereto as long as it is a method which can form a thin film. A solution containing an emitting dopant and host material is applied in a desired thickness, followed by heating and drying with a hot plate and the like. The solution to be applied may be filtrated with a filter in advance.

The thickness of the emissive layer 14 is preferably 10-100 nm. The ratio of the host material and emitting dopant in the emissive layer 14 is arbitrary as long as the effect of the present invention is not impaired.

The substrate 11 is a member for supporting other members. The substrate 11 is preferably one which is not modified by heat or organic solvents. A material of the substrate 11 includes, for example, an inorganic material such as alkali-free glass and quartz glass; plastic such as polyethylene, polyethylene terephthalate (PET), polyethylene naphthalate (PEN), polyimide, polyamide, polyamide-imide, liquid crystal polymer, and cycloolefin polymer; polymer film; and metal substrate such as stainless steel (SUS) and silicon. In order to obtain light emission, a transparent substrate consisting of glass, synthesized resin, and the like is preferably used. Shape, structure, size, and the like of the substrate 11 are not particularly limited, and can be appropriately selected in accordance with application, purpose, and the like. The thickness of the substrate 11 is not particularly limited as long as it has sufficient strength for supporting other members.

The anode 12 is formed on the substrate 11. The anode 12 injects holes into the hole transport layer 13 or the emissive layer 14. A material of the anode 12 is not particularly limited as long as it exhibits conductivity. Generally, a transparent or semitransparent material having conductivity is deposited by vacuum evaporation, sputtering, ion plating, plating, and coating methods, and the like. For example, a metal oxide film and semitransparent metallic thin film exhibiting conductivity may be used as the anode 12. Specifically, a film prepared by using conductive glass consisting of indium oxide, zinc oxide, tin oxide, indium tin oxide (ITO) which is a complex thereof, fluorine doped tin oxide (FTO), indium zinc oxide, and the like (NESA etc.); gold; platinum; silver; copper; and the like are used. In particular, it is preferably a transparent electrode consisting of ITO. As an electrode material, organic conductive polymer such as polyaniline, the derivatives thereof, polythiophene, the derivatives thereof, and the like may be used. When ITO is used as the anode 12, the thickness thereof is preferably 30-300 nm. If the thickness is thinner than 30 nm, the conductivity is decreased and the resistance is increased, resulting in reducing the luminous efficiency. If it is thicker than 300 nm, ITO loses flexibility and is cracked when it is under stress. The anode 12 may be a single layer or stacked layers each composed of materials having various work functions.

The hole transport layer 13 is optionally arranged between the anode 12 and emissive layer 14. The hole transport layer 13 receives holes from the anode 12 and transports them to the emissive layer side. As a material of the hole transport layer 13, for example, polythiophene type polymer such as a conductive ink, poly(ethylenedioxythiophene):polystyrene sulfonate [hereinafter, referred to as PEDOT:PSS] can be used, but is not limited thereto. A method for forming the hole transport layer 13 is not particularly limited as long as it is a method which can form a thin film, and may be, for example, a spin coating method. After applying a solution of hole transport layer 13 in a desired film thickness, it is heated and dried with a hotplate and the like. The solution to be applied may be filtrated with a filter in advance.

The electron transport layer 15 is optionally formed on the emissive layer 14. The electron transport layer 15 receives electrons from the electron injection layer 16 and transports them to the emissive layer side. As a material of the electron transport layer 15 is, for example, tris[3-(3-pyridyl)-mesityl]borane [hereinafter, referred to as 3TPYMB], tris(8-hydroxyquinolinato)aluminum [hereinafter, referred to as Alq$_3$], and basophenanthroline (BPhen), but is not limited thereto. The electron transport layer 15 is formed by vacuum evaporation method, a coating method or the like.

The electron injection layer 16 is optionally formed on the electron transport layer 15. The electron injection layer 16 receives electrons from the cathode 17 and transports them to the electron transport layer 15 or emissive layer 14. A material of the electron injection layer 16 is, for example, CsF, LiF, LiQ, Ba, BaO, Ca and the like, but is not limited thereto. The electron injection layer 16 is formed by vacuum evaporation method, a coating method or the like.

The cathode 17 is formed on the emissive layer 14 (or the electron transport layer 15 or the electron injection layer 16). The cathode 17 injects electrons into the emissive layer 14 (or the electron transport layer 15 or the electron injection layer 16). Generally, a transparent or semitransparent material having conductivity is deposited by vacuum evaporation, sputtering, ion plating, plating, coating methods, and the like. Materials for the cathode include a metal oxide film and semitransparent metallic thin film exhibiting conductivity. When the anode 12 is formed with use of a material having high work function, a material having low work function is preferably used as the cathode 17. A material having low work function includes, for example, alkali metal and alkali earth metal. Specifically, it is Li, In, Al, Ca, Mg, Na, K, Yb, Cs, Ag and the like.

The cathode 17 may be a single layer or stacked layers each composed of materials having various work functions. Further, it may be an alloy of two or more metals. Examples of the alloy include a lithium-aluminum alloy, lithium-magnesium alloy, lithium-indium alloy, magnesium-silver alloy, magnesium-indium alloy, magnesium-aluminum alloy, indium-silver alloy, and calcium-aluminum alloy.

The thickness of the cathode 17 is preferably 10-150 nm. When the thickness is thinner than the aforementioned range, the resistance is excessively high. When the film thickness is thicker, long period of time is required for deposition of the cathode 17, resulting in deterioration of the performance due to damage to the adjacent layers.

Explained above is an organic light-emitting diode in which an anode is formed on a substrate and a cathode is arranged on the opposite side to the substrate, but the substrate may be arranged on the cathode side.

Figure 2:
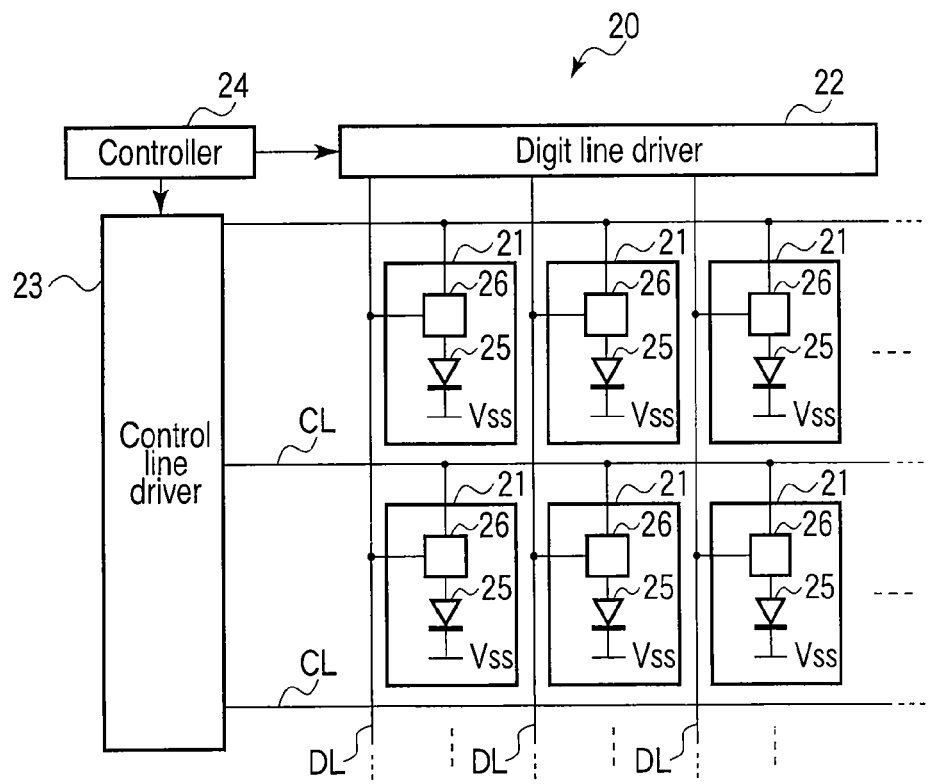
FIG. 2 is a circuit diagram showing a display of an embodiment.

FIG. 2 is a circuit diagram showing a display according to an embodiment.

A display 20 shown in FIG. 2 has a structure in which pixels 21 are arranged in circuits each provided with a lateral control line (CL) and vertical digit line (DL) which are arranged matrix-wise. The pixel 21 includes a light-emitting diode 25 and a thin-film transistor (TFT) 26 connected to the light-emitting diode 25. One terminal of the TFT 26 is connected to the control line and the other is connected to the digit line. The digit line is connected to a digit line driver 22. Further, the control line is connected to the control line driver 23. The digit line driver 22 and the control line driver 23 are controlled by a controller 24.

Figure 3:
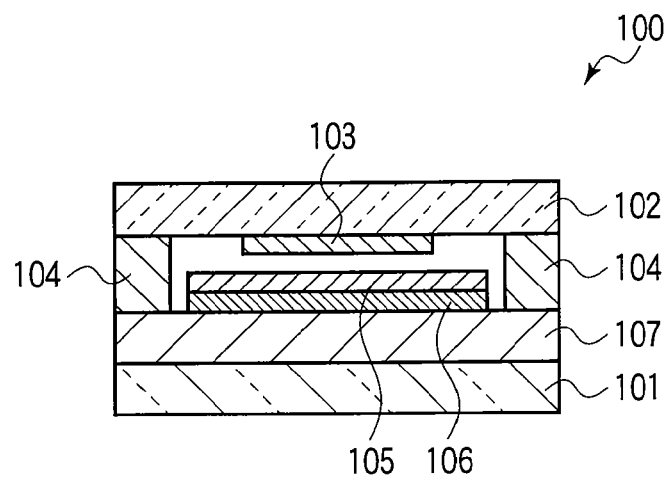
FIG. 3 is a cross-sectional view showing a lighting device of an embodiment.

FIG. 3 is a cross-sectional view showing a lighting device according to an embodiment.

A lighting device 100 has a structure in which an anode 107, an organic light-emitting diode layer 106 and a cathode 105 are formed in this order on a glass substrate 101. A seal glass 102 is disposed so as to cover the cathode 105 and adhered using a UV adhesive 104. A drying agent 103 is disposed on the cathode 105 side of the seal glass 102.

EXAMPLES

Synthesis of [CuBr(PyC2PPh$_2$)(PPh$_3$)]

A 100 mL recovery flask was charged with copper bromide (I) dimethylsulfide (69.8 mg, 0.34 mmol) and 2-(2-diphenylphosphino)ethyl)pyridine (PyC2PPh$_2$) (99.1 mg, 0.34 mmol), and the mixture in the flask was dried under vacuum. The atmosphere of the recovery flask was purged with nitrogen, and 20 mL of chloroform bubbled by nitrogen was added in the flask by using a syringe in which the atmosphere was purged with nitrogen. After the mixture was stirred at ambient temperature for 6 hours, vacuum-dried triphenylphosphine (88.7 mg, 0.34 mmol) was added. After the mixture was stirred at ambient temperature for further 6 hours, the reaction solution was filtrated to remove insoluble materials. After evaporating the solvent of the filtrate, a solid was precipitated by drying under vacuum. The obtained solid was dissolved into chloroform (rich solvent), and diethylether (poor solvent) was slowly added while being diffused, whereby a white solid was precipitated. The precipitate was isolated by filtration to obtain [CuBr(PyC2PPh$_2$)(PPh$_3$)] which was a target product (yield 88%).

A reaction scheme of the above-described synthetic reaction is shown below.

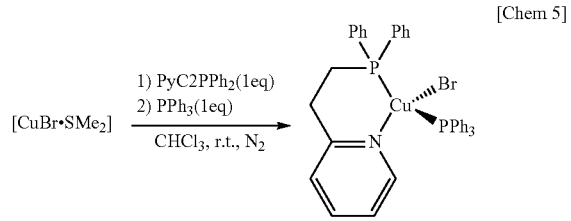

[Chem 5]

Figure 4:
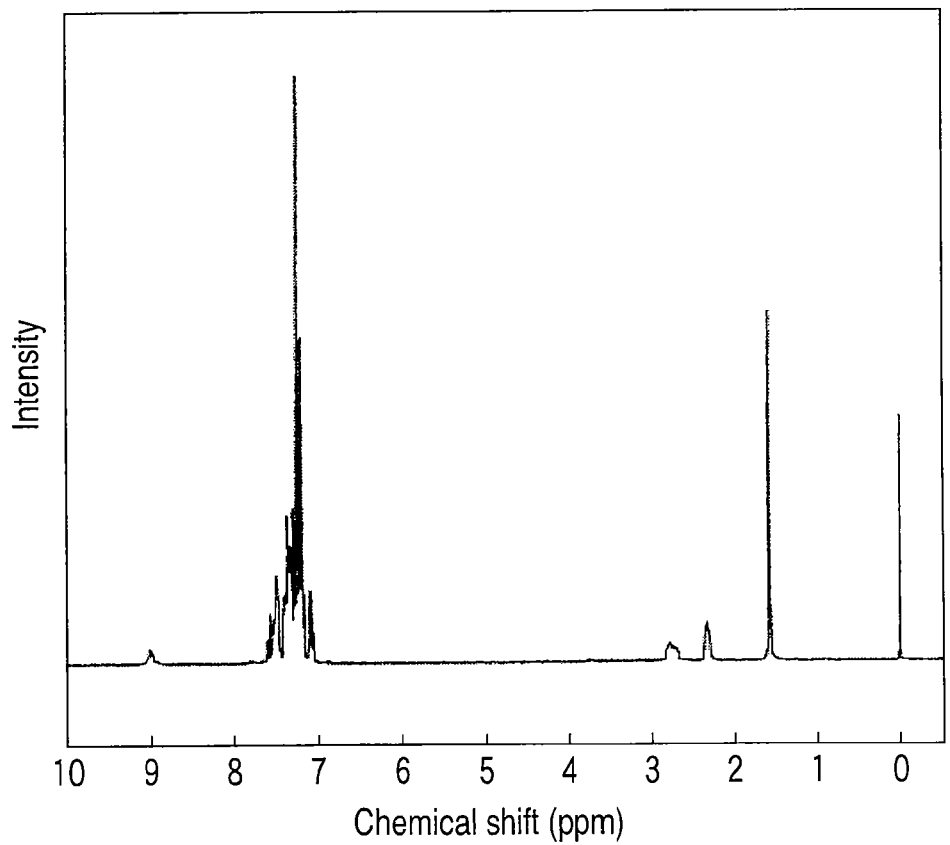
FIG. 4 is a view showing the $^1$H-NMR spectrum of [CuBr(PyC2PPh$_2$)(PPh$_3$)]

$^1$H-NMR spectrum (CDCl$_3$, 270 MHz) of [CuBr(PyC2PPh$_2$)(PPh$_3$)] synthesized by the above-described method is shown in FIG. 4.

Fabrication of Organic Light-Emitting Diode

The above synthesized [CuBr(PyC2PPh$_2$)(PPh$_3$)] was used as an emitting dopant to fabricate an organic light-emitting diode. The layer structure of this diode is as follows: ITO 100 nm/PEDOT:PSS 45 nm/PVK:OXD-7:[CuBr(PyC2PPh$_2$)(PPh$_3$)] 70 nm/3TPYMB 25 nm/CsF 1 nm/Al 150 nm.

The anode was a transparent electrode made of ITO (indium-tin oxide) 100 nm in thickness.

As the material of the hole-transport layer, an aqueous poly(ethylenedioxythiophene):poly(styrene.sulfonic acid) [PEDOT:PSS] solution which is conductive ink was used. An aqueous PEDOT:PSS solution was applied by spin coating, and dried under heating to form a hole-transport layer 45 nm in thickness.

As to the materials used for the emissive layer, a poly(N-vinylcarbazole) [PVK] was used as the host material, 1,3-bis(2-(4-tertiarybutylphenyl)-1,3,4-oxydiazole-5-yl)benzene [OXD-7] was used as the electron-transport material and [CuBr(PyC2PPh$_2$)(PPh$_3$)] was used as the emitting dopant. PVK is a hole-transport host material and OXD-7 is an electron-transport material. Therefore, if a mixture of these materials is used as the host material, electrons and holes can be efficiently injected into the emissive layer when voltage is applied. These compounds were weighed such that the ratio by weight of these compounds is as follows: PVK:OXD-7:[CuBr(PyC2PPh$_2$)(PPh$_3$)]=60:30:10, and dissolved in chlorobenzene to obtain a solution, which was applied by spin coating, followed by drying under heating to form an emissive layer 70 nm in thickness.

The electron-transport layer was formed in a thickness of 50 nm by vapor evaporation of tris[3-(3-pyridyl)-mesityl]borane [3TPYMB]. The electron injection layer was formed of CsF 1 nm in thickness and the cathode was formed of Al 150 nm in thickness.

Measurement of Electroluminescence Spectrum

Figure 5:
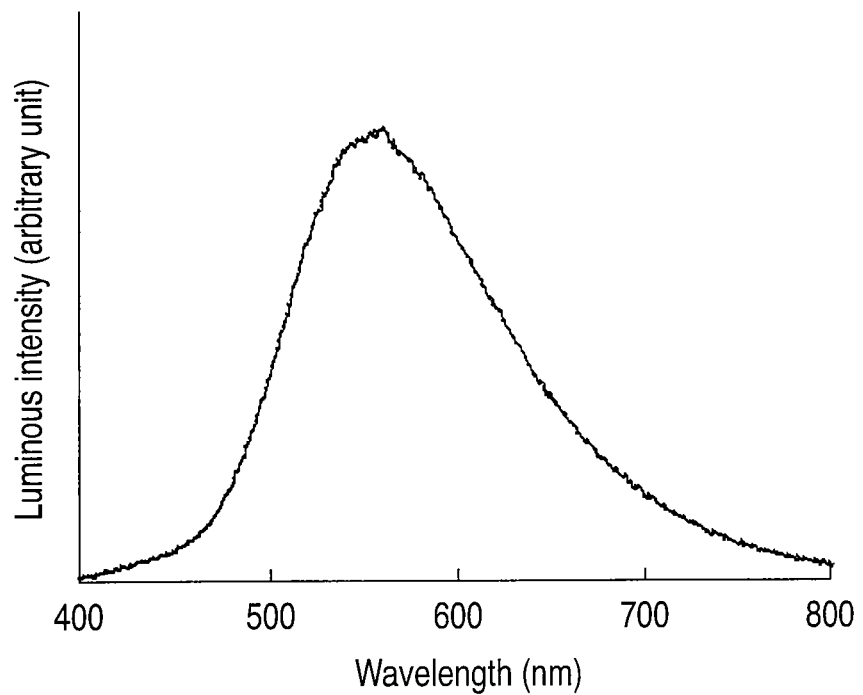
FIG. 5 is a view showing the electroluminescence spectrum of an organic light-emitting diode according to Example.

An electroluminescence spectrum at a voltage application of the organic light-emitting diode produced as described above was measured. The measurement was conducted by using a high sensitivity multi-channel spectroscope C10027-01 manufactured by Hamamatsu Photonics K.K. The results are shown in FIG. 5. An electroluminescence spectrum having an emission peak at 560 nm was obtained.

Luminous Characteristics of Organic Light-Emitting Diode

Figure 6A:
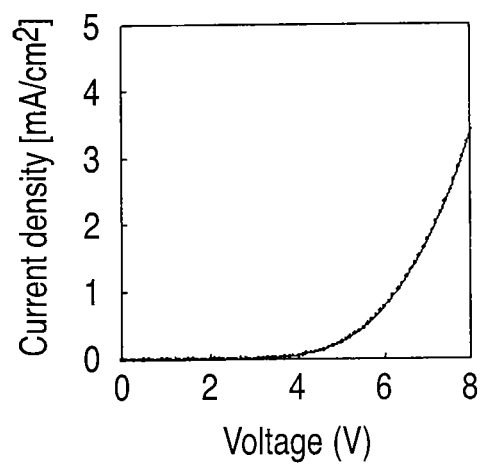
FIG. 6A is a view showing the relationship between the voltage and current density of the diode according to Example.
Figure 6B:
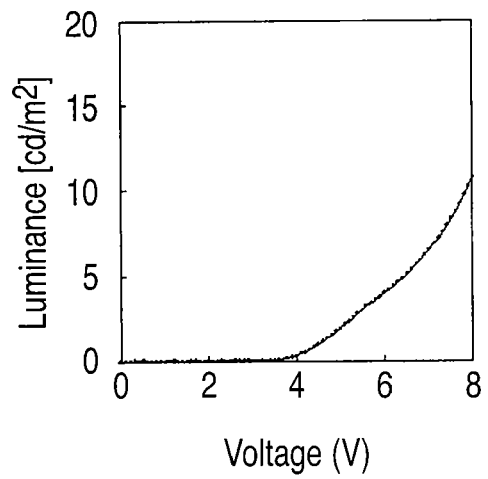
FIG. 6B is a view showing the relationship between the voltage and luminance of the diode according to Example.

The luminous characteristics of the organic light-emitting diode fabricated in the above manner were examined. FIG. 6A is a view showing the relationship between the voltage and current density of the diode according to Example. FIG. 6B is a view showing the relationship between the voltage and luminance of the diode according to Example. The luminance was measured using an Si Photodiode S7610 (trade name, manufactured by Hamamatsu Photonics K.K.) with a visibility filter. Further, the current and the voltage were measured using a Semiconductor Parameter Analyzer 4156b (trade name, manufactured by Hewlett Packard).

Current density rose along with application of voltage and the light-emitting was started at 4.5 V. In contract, a turn-on voltage of an organic light-emitting diode using the copper complex disclosed in Optical Materials; 2007; 29; 667-671 cited as a prior art document is 10 V. Therefore, the turn-on voltage of the organic light-emitting diode of the present example was reduced by about 5.0 V as compared to the organic light-emitting diode of the prior art document. In this specification, "a turn-on voltage" means a threshold voltage for starting emission. Also, luminance of the organic light-emitting diode of the present example was 10 cd/cm$^2$ at 8 V.

According to the embodiment or the examples, it is possible to provide the copper complex which is inexpensive, is easily synthesized and capable of starting emission with a low applied voltage when used as an emitting dopant of an organic light-emitting diode. Also, it is possible to provide the organic light-emitting diode, the display device and the lighting device using the copper complex as the emitting dopant.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A compound represented by Formula (1):

[Chem 1]

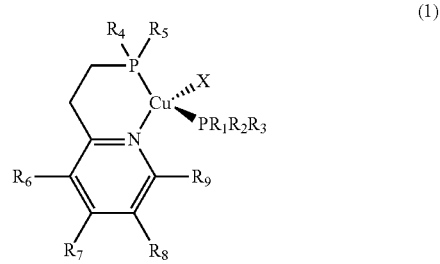

(1)

where

Cu represents a copper;

PR$_1$R$_2$R$_3$ represents a phosphine compound coordinating with Cu, where R$_1$, R$_2$ and R$_3$ may be the same or different, and represent a linear, branched or cyclic alkyl group having 1-6 carbon atoms or an aromatic cyclic group which may have a substituent;

R$_4$ and R$_5$ may be the same or different, and represent a linear, branched or cyclic alkyl group having 1-6 carbon atoms or an aromatic cyclic group which may have a substituent;

R$_6$, R$_7$, R$_8$ and R$_9$ each independently represents a halogen atom, cyano group, nitro group, linear, branched or cyclic alkyl group having 1-6 carbon atoms or H; and X represents F, Cl, Br or I.

2. The compound according to claim 1, wherein
each of R$_1$, R$_2$, R$_3$, R$_4$ and R$_5$ represents a phenyl group,
each of R$_6$, R$_7$, R$_8$ and R$_9$ represents H, and
X represents Br.

3. An organic light-emitting diode comprising:
an anode and a cathode which are arranged apart from each other; and
an emissive layer interposed between the anode and the cathode and comprising a host material and an emitting dopant, the emitting dopant comprising the compound according to claim 1.

4. The light-emitting diode according to claim 3, wherein the host material is a small-molecular material or a polymer material.

5. A display comprising the organic light-emitting diode according to claim 3.

6. A lighting device comprising the organic light-emitting diode according to claim 3.

* * * * *